United States Patent [19]
Yoder, Jr.

[11] Patent Number: 4,902,123
[45] Date of Patent: Feb. 20, 1990

[54] TOPOGRAPHY MEASURING APPARATUS
[75] Inventor: Paul R. Yoder, Jr., Wilton, Conn.
[73] Assignee: Taunton Technologies, Inc., Monroe, Conn.
[21] Appl. No.: 125,240
[22] Filed: Nov. 25, 1987
[51] Int. Cl.$^4$ .............................................. A61B 3/10
[52] U.S. Cl. ..................................... 351/212; 351/247
[58] Field of Search ..................... 351/212, 247, 205; 356/124

[56] References Cited

U.S. PATENT DOCUMENTS

| | | |
|---|---|---|
| 3,937,566 | 2/1976 | Townsley . |
| 4,019,813 | 4/1977 | Cornsweet et al. . |
| 4,157,859 | 6/1979 | Terry . |
| 4,159,867 | 7/1979 | Achatz et al. . |
| 4,180,325 | 12/1979 | Humphrey . |
| 4,182,572 | 1/1980 | Humphrey . |
| 4,213,678 | 7/1980 | Pomerantzeff et al. . |
| 4,251,139 | 2/1981 | Matsumura . |
| 4,252,420 | 2/1981 | Kohayakawa . |
| 4,253,743 | 3/1981 | Matsumura . |
| 4,256,384 | 3/1981 | Kani et al. . |
| 4,259,589 | 3/1981 | DiMatteo et al. . |
| 4,265,518 | 5/1981 | Matsumura . |
| 4,272,190 | 6/1981 | Shapiro . |
| 4,312,574 | 1/1982 | Wilms . |
| 4,355,871 | 10/1982 | Nevyas ................. 351/237 |
| 4,372,655 | 2/1983 | Matsumura et al. ......... 351/206 |
| 4,407,572 | 10/1983 | Humphrey .............. 351/212 |
| 4,429,960 | 2/1984 | Mocilac et al. ............ 351/212 |
| 4,439,025 | 3/1984 | Smirmaul ................ 351/212 |
| 4,440,477 | 4/1984 | Schachar ................ 351/212 |
| 4,469,416 | 9/1984 | Isono .................... 351/206 |
| 4,490,022 | 12/1984 | Reynolds ................ 351/211 |
| 4,494,838 | 1/1985 | Wallquist et al. .......... 351/206 |
| 4,523,821 | 6/1985 | Lang et al. .............. 351/214 |
| 4,540,254 | 9/1985 | Humphrey ............... 351/212 |
| 4,544,248 | 10/1985 | Nunokawa ............... 354/62 |
| 4,569,576 | 2/1986 | Karpov et al. ............ 351/212 |
| 4,572,628 | 2/1986 | Nohda .................. 351/212 |
| 4,579,430 | 4/1986 | Bille ................... 351/206 |
| 4,582,404 | 4/1986 | Hamilton ............... 351/212 |
| 4,588,270 | 5/1986 | Tamaki ................. 351/212 |
| 4,626,089 | 12/1986 | Takahashi et al. ......... 351/208 |
| 4,641,349 | 2/1987 | Flom et al. .............. 382/2 |
| 4,660,946 | 4/1987 | Nakamura et al. ......... 351/212 |
| 4,660,947 | 4/1987 | Amoils ................. 351/212 |
| 4,662,730 | 5/1987 | Outwater et al. ......... 351/212 |
| 4,665,913 | 5/1987 | L'Esperance . |
| 4,666,269 | 5/1987 | Nakamura et al. ......... 351/212 |
| 4,669,466 | 6/1987 | L'Esperance . |
| 4,673,264 | 6/1987 | Takahashi .............. 351/211 |
| 4,679,919 | 7/1987 | Itoh et al. ............... 351/206 |
| 4,685,140 | 8/1987 | Mount, II ............... 351/212 |
| 4,692,003 | 9/1987 | Adachi et al. ............ 351/212 |
| 4,699,482 | 10/1987 | Utsugi ................. 351/206 |
| 4,710,003 | 12/1987 | Masuda et al. ........... 351/212 |
| 4,718,418 | 1/1988 | L'Esperance . |
| 4,721,379 | 1/1988 | L'Esperance . |
| 4,740,071 | 4/1988 | Kobayashi .............. 351/206 |
| 4,743,107 | 5/1988 | Aizu et al. .............. 351/221 |
| 4,747,683 | 5/1988 | Doane .................. 351/206 |
| 4,761,071 | 8/1988 | Baron .................. 351/212 |

Primary Examiner—Rodney B. Bovernick
Attorney, Agent, or Firm—Kramer, Brufsky & Cifelli

[57] ABSTRACT

A contour measuring apparatus and method of using the apparatus is disclosed to measure the three-dimensional contour of a surface. A multi-point light source directs a plurality of light beams onto the surface to be measured. The light beams are reflected through a lens onto a photodetector to produce electro-optically measurable optical images. A structure is provided to determine the local radius of curvature of the surface at each desired point of incidence of individual light beams and the three-dimensional surface contour of the surface being measured. A calibration device is provided to reduce instrument errors of the apparatus. The calibration device includes a calibration surface with a known contour to be positioned in substitution of the surface being measured. The apparatus includes a structure to sequentially determine and store a memory of the location of the calibration surface and to compare the reflection of the light from the calibration surface as well as the surface being measured to determine the contour of the surface being measured.

35 Claims, 5 Drawing Sheets

TOPOGRAPHY MEASURING APPARATUS

BACKGROUND OF THE INVENTION

While the invention is subject to a wide range of applications, it is particularly suited to measure the three-dimensional contour of a surface. In particular, this invention relates to that aspect of ophthalmic diagnosis which is concerned with measurement of the three-dimensional contour of the anterior surface of the cornea. This measurement discloses abnormalities in the cornea which may have deleterious effects upon vision or quantifies progress of ophthalmic surgery, such as laser-aided radial keratotomy or laser ablation of the external surface of the cornea with penetration into the stroma and volumetric removal of tissue, whereby the external corneal surface is characterized by a sculptured, new curvature having improved optical properties.

Devices variously called corneascopes or keratometers have been developed for topographic analysis of the cornea. Such devices have found acceptance as means for measuring corneal curvature in preparation for prescribing a contact lens to be worn over the measured cornea to reduce certain visual defects, or for use in other ophthalmic applications. The prior art for these devices entails photographic (as in U.S. Pat. No. 3,797,921, Kilmer, et al.) or electro-optical (see U.S. Pat. No. 4,572,628, Nohda) recording of cornea-reflected images of illuminated objects comprising several concentric rings, or multiple discrete light sources arranged in the form of concentric rings, on a flat surface normal to the optical system axis or on a concave surface symmetrically disposed with respect to that axis. If the cornea is spherical, the reflected images of these ring-shaped objects are equally spaced, continuous or intermittent, concentric ring-shaped patterns. If the cornea surface is rotationally symmetrical but not spherical, the resultant ring images are less equally spaced; the inequality of spacing is thus a measure of nonsphericity of the cornea surface. If the cornea surface is astigmatic, as is frequently the case, the ring-shaped images reflected by that cornea will appear elliptical, and the eccentricity of the pattern is related to the change in curvature of the cornea surface between various sectional meridians. This eccentricity, and hence the astigmatism of the surface, can be measured by careful analysis of an image of the ring pattern. The orientation of the major and minor axes of the elliptical pattern relative to the eye indicates the orientation of the principal axes of the observed astigmatism. If the cornea has been warped or distorted by injury, by disease or by prior surgical procedures, such as radial keratotomy or imperfect closure of incisions made during cataract or other surgery, the magnitudes of these surface defects can also be measured.

In each of these described cases, the desired end result is (1) a tabular or graphic representation of the surface optical power (in units of diopters) at various points over the visually used, central portion of the cornea (typically 3 to 7 mm in diameter), and (2) computed average values for these parameters over the area of interest. Because of the tendency for the eye to become astigmatic, or non-rotationally symmetrical, comparisons of surface radius or power are frequently made for various azimuthal meridians about the visual axis. Instrument errors introduced by the apparatus and systematic or random errors introduced by the method of use are preferably minimized in order to minimize the overall measurement error. Prior art devices for accomplishing these measurements have been found lacking in regard to one or more of the following attributes: accuracy, ease of use, and time required to obtain the desired tabular or graphical output. None of these devices is compatible with use in situ and in close temporal alignment with surgical laser sculpturing of the cornea to produce desired net curvature changes to improve vision.

BRIEF STATEMENT OF THE INVENTION

It is an object of the invention to provide a method and means for improving the accuracy and speed with which the topography of the anterior surface of the cornea can be measured.

It is a specific object to meet the above object by incorporating a self-calibration capability which ensures that the instrument error of the measurement is small.

It is another object to incorporate a simple means for achieving proper location and orientation of the eye under test with respect to the diagnostic apparatus.

A further specific object is to make possible the measurement of corneal radius, and thus optical power, at individual small, localized areas on the surface.

Another object is to provide an in situ means for observing the exterior of the eye and for measuring the topography of the cornea surface at selected times before, during and after performance of surgical procedures such as are taught by pending L'Esperance, Jr. patent applications including Ser. No. 691,923, Ser. No. 748,358, Ser. No. 891,169 and Ser. No. 891,285.

Those applications cover the ablation of the cornea with penetration into the stroma and volumetric removal of corneal tissue through controlled application of radiation from an ultraviolet laser, or similar procedures utilizing radiation of longer wavelength such as an infrared laser operating at about 2.9 micrometers.

The invention achieves the foregoing objects by analyzing the pattern of images of an array of light points specularly reflected from the surface being measured such as the convex surface formed by a cornea being measured for diagnostic purposes or, for example, a spherical ball of known radius of curvature used for apparatus calibration purposes. In a preferred embodiment, the apparatus is capable of interfacing directly with apparatus as described by Telfair, et al., in pending patent applications Ser. No. 938,633 and Ser. No. 009,724, so as to permit diagnostic evaluation of a given cornea in conjunction with surgical sculpturing of the same cornea with laser radiation to improve its optical properties.

BRIEF DESCRIPTION OF THE DRAWINGS

The invention will be illustratively described for preferred and other embodiments, in conjunction with the accompanying drawings, in which.

DETAILED DESCRIPTION OF THE INVENTION

A contour measuring apparatus 9 to measure the three-dimensional contour of a surface 13 is disclosed. The apparatus 9 includes a multi-point light source 11 to direct a plurality of individual light beams 10 onto the surface 13. A photodetector 19 produces electro-optically measurable optical images. A lens 15 is disposed between the surface 13 and the photodetector 19 to focus the reflected beams of light 14 from the surface being measured 13 onto the photodetector 19 to form the measurable optical images. A signal switch 21, a frame grabber 23, and computer means 24 are in electrical communication with said photodetector 19 for determining both the local radius of curvature of the surface 13 at each desired point of incidence of the individual light beams and the three-dimensional contours of the surface 13. A calibration device 70 is provided to reduce instrument errors of the apparatus 9. The calibration device 70 includes a calibration surface 72 with a known contour to be positioned in substitution of the surface 13 being measured. Components 21 and 23 sequentially determine and store in memory the location on said calibration surface 71 of each image of individual light points. Means 24 further determine the contour of the surface 13 being measured from a differential evaluation of the reflection of each light point image from the surface 13 being measured in comparison to the reflection of each light point image from the calibration surface 71 with a known contour.

Figure 1:
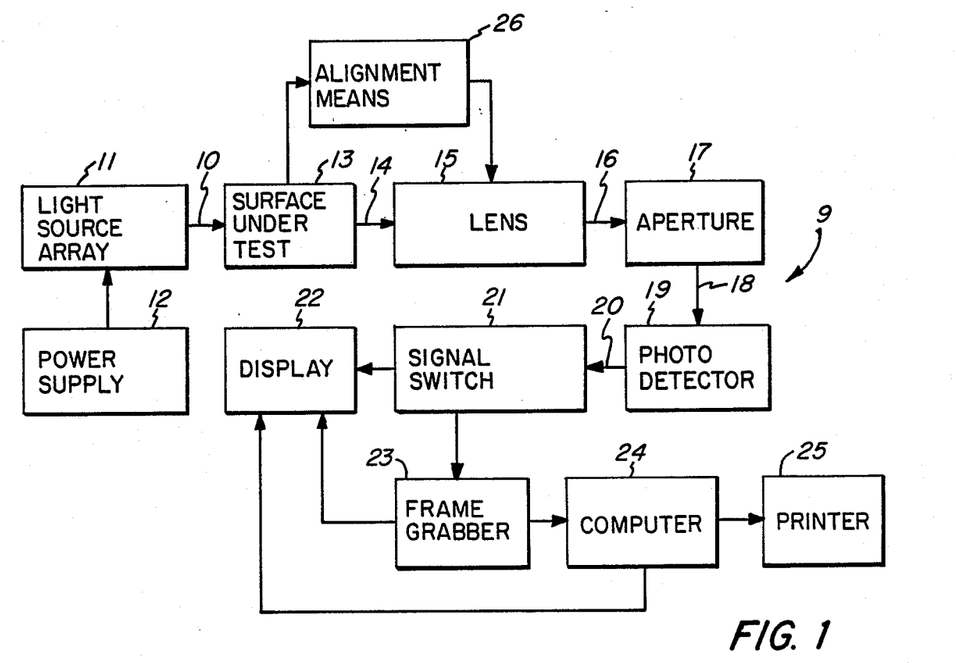
FIG. 1 is a simplified block diagram to show the functional relationships of generalized optical, mechanical and electrical components of topography-measuring apparatus of the invention.

In FIG. 1, the invention is shown as an apparatus 9 for producing and interpreting images reflected from a surface under test. An array 11 of light sources is activated by a power supply 12, and multiple diverging light beams 10 from the array are intercepted by a contoured surface 13 under test; contoured surface 13 acts as a mirror to reflect light beams 14 into a lens 15 which, in turn, focuses those light beams 16 through an aperture or iris 17. The beams 18 emerging from aperture 17 are then focused onto the sensitive surface of a photodetecting means 19. Electrical output signals 20 generated by means 19 are directed by a signal switch 21 to a frame grabber 23 which produces a time-sequenced series of electrical signals representative of the spatial distribution of energy in the image formed by lens 15. These electrical signals can be displayed as a real time video image in a display apparatus 22. Alternatively or in addition, the electrical signals can be stored in digital form by a frame grabber 23, for further analysis by a computer 24 and/or for supply to display means 22 or print-out means 25. Special algorithms stored in computer 24 permit computation of the radius of curvature, and hence of the optical power, of contoured surface 13 at the point of incidence on said surface of the beam from any one light source in the array 11. Means 26 allows the optical alignment of the surface 13 relative to the axis of lens 15 to be measured.

Figure 2:
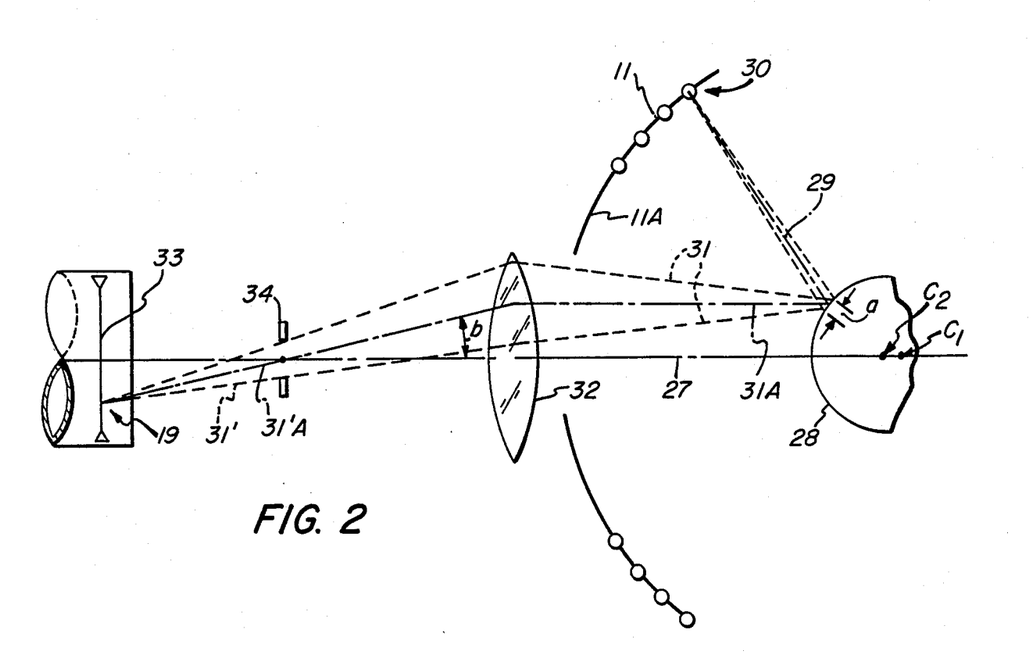
FIG. 2 is a diagram of principal optical components of FIG. 1, including an array of multiple light sources.

Further detail as to function of the involved optical system of the invention is shown in FIG. 2, wherein the array 11 comprises a plurality of individual light emitting diodes (LEDS) disposed on a nominally spherical surface 11A, of known contour, having its center $C_1$ on the optical axis 27 of the system. Preferably, the surface 11A is nominally spherical; however, it is within the terms of the invention for the surface 11A to be of any desired shape. Although the array 11 of light sources preferably is comprised of LEDs, it is also within the terms of the present invention to construct the array 11 of any type of light sources, such as a plurality of fiber optics. The center $C_2$ of a convex surface 28, equivalent to surface 13 in FIG. 1, under test also lies on the axis 27 but does not necessarily coincide with $C_1$. One of the beams 10 is the divergent beam 29 from a typical LED 30 which is redirected, upon reflection from surface 28, as a more divergent beam 31 of the beams 14 into the aperture of a lens 32. The lens 32 is preferably centered on axis 27 and located at an appropriate distance downstream from surface 28. Through the image-forming properties of lens 32, an image of the typical LED 30 is produced at some point on the photocathode 33 of a conventional photo-detecting device 19 which may be a vidicontype image tube; alternatively, device 19 may be an array of discrete detectors such as a charge coupled device (CCD). Typically, the photocathode of such an image tube or array would have usable aperture dimensions of about 6.6×8.8 mm and would be sensitive to the visible light emitted by the light source 11. Because of the inherent rotational symmetry of the various optical and electro-optical components about the axis 27, the image of the entire array 11 typically lies within a circle inscribed within the rectangular usable aperture of the photocathode. It should be noted that the photodetector means 19 is in no way limited to the indicated light source or particular dimensions, in that larger or smaller devices of like or different nature may be accommodated by selection of the specific type of photodetector 19 and by appropriately scaling the size of the image.

A feature of the invention is the inclusion of an aperture such as iris 34 located on the axis 27, offset from lens 32 at a distance substantially equal to the back focal length (BFL) of the lens 32, thus placing iris 34 at the focal point of the lens. The opening of iris 34 is constrained to always be small enough that it, rather than the aperture of lens 32, determines the angular size of the conical beam 31' of beam 18. The iris 34 acts as the aperture stop of the system and controls the cone angle of the individual beams 14, 16, 18, 31', 31 and 29 as well as the size of the area "a" on test surface 28 which contributes light from the typical LED 30 to the corresponding image point on photodetecting means 19. Since iris 34 is located at the focal point of lens 32, light rays 31'A passing centrally through the iris, at any angle "b" with respect to axis 27, must propagate parallel to axis 27 in the space between test surface 28 and lens 32. These rays 31'A, called principal rays, are then said to be telecentric in the object space of lens 32, and the aperture stop 34, i.e., the iris, is a telecentric stop. The opening in the iris 34 can be small since the LEDs are intrinsically very bright and the image sensor is very sensitive to incident light. All the rays in the beam from a given LED are therefore physically near each other and all closely approximate the path of the appropriate principal ray.

The fact that the principal rays from all LEDs in the array 11 travel parallel to axis 27, after reflecting from surface 28, allows use of a simple mathematical process to independently compute the average radius of surface 28 over each of the small localized areas of dimension "a" centered about the intercept points of the principal rays on surface 28.

Figure 3:
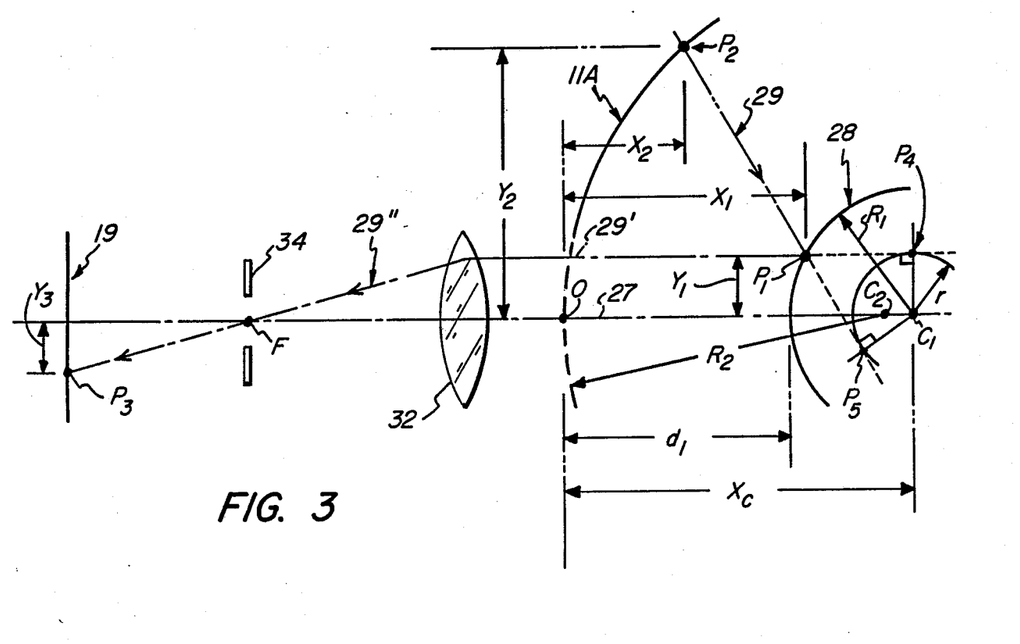
FIG. 3 is a diagram showing certain geometric relationships that are pertinent to the optical arrangement of FIG. 2.

FIG. 3 illustrates the applicable geometrical condition. It may be noted that surface 28 is located at an axial distance $d_1$ from surface 11A and that the principal ray 29 from a typical LED 30 (here assumed to be a point source of light at $P_2$) intercepts surface 28 at a height $Y_1$ from the axis 27 and proceeds to lens 32 as ray 29' parallel to said axis. Ray 29' becomes ray 29" beyond lens 32 and passes through focal point F in its place route to point $P_3$ at the image plane within the image sensor 19. The radial distance $Y_3$ of $P_3$ from the axis 27 is related to $Y_1$ by the lateral magnification ratio inherent in the lens 32. A method for determining this magnification ratio is described later in this description.

The law of reflection at an optical surface requires the path of ray 29 from $P_2$ to $P_1$ to be such that (a) its extension (dashed line) through surface 28 and (b) the extension (dashed line) of reflected ray 29' are both tangent (at $P_5$ and $P_4$, respectively) to a circle constructed concentric with surface 28. The perpendicular distance from tangent point $P_4$ to center $C_1$ thus equals the perpendicular distance from tangent point $P_5$ to that same center. For convenience, both of these distances will be referred to as "r", which may be expressed:

$$r = \frac{AX_c + BY_c + C}{\sqrt{A^2 + B^2}} ; \quad (1)$$

where:
$A = Y_1 - Y_2$, $B = X_2 - X_1$, and $C = X_2 Y_1 - X_1 Y_2$ and $X_c$, $Y_c$ are the coordinates of center $C_1$ measured from X and Y axes through origin "0" at surface 11A. Since ray 29' is parallel to axis 27, as shown in FIG. 3, r also equals $Y_1$. In the nominal case, $Y_c = 0$, since $C_1$ lies on the X axis.

As mentioned in connection with FIG. 1, the image on the photodetector 19 can be analyzed mathematically. A frame of multiple LED images can be stored digitally by frame grabber 23 for subsequent analysis in computer 24 and display at 22. The results of the analysis can be tabulated and various representations of the surface contour printed by printer 25. The information needed to compute the radius of curvature of the surface 28 at various points comprises the radial distance $Y_3$ for each of the images of the LEDs in array 11. Since the magnification ratio of lens 32 can be determined, the corresponding heights $Y_1$ can be computed.

When the coordinates of $P_2$ and of $C_1$ and the Y coordinate of $P_1$ are known, the unique value of $X_1$ can be computed from the quadratic equation:

$$X_1 = \frac{-E \pm \sqrt{E^2 - 4DG}}{2D} ; \quad (2)$$

where:
$D = A(2Y_1 - A)$, $E = 2A(A X_c - X_c Y_1 - X_2 Y_1)$, and $G = A^2(Y_1^2 - X_c^2) + 2A X_c X_2 Y_1$ Once $X_1$ and $Y_1$ are known, the radius $R_1$ at $P_1$ can be computed from the expression:

$$R_1 = \sqrt{Y_1^2 + X_1^2} \quad (3)$$

In general, the axial distance $d_1$ between the surfaces 11A and 28 can be measured by standard means. Hence, $$X_c = d_1 + R_1 \quad (4)$$

Since radius $R_1$ is initially unknown, an iterative procedure may be used wherein a reasonable value for $R_1$ is chosen and substituted into Equation 4 to give a first approximation for $X_c$. Then, values of the coefficients A, D, E and G are determined, and a first approximation value for $R_1$ is computed from Equation 3. Successive computations give progressively more precise values for $R_1$; the iterative process is stopped when the desired precision is achieved.

This mathematical process is repeated for each LED image, and the local radius of the cornea is computed, for each of the various locations intercepted by narrow beams from the individual LEDs. The average radius of the surface, the extreme long and short radii of said surface, the dioptric equivalent of each of these radii, and the difference in average optical powers in the directions of the principal astigmatic meridians, as well as the azimuthal orientations of said meridians, can then be determined using methods of analytic geometry.

Figure 4A:
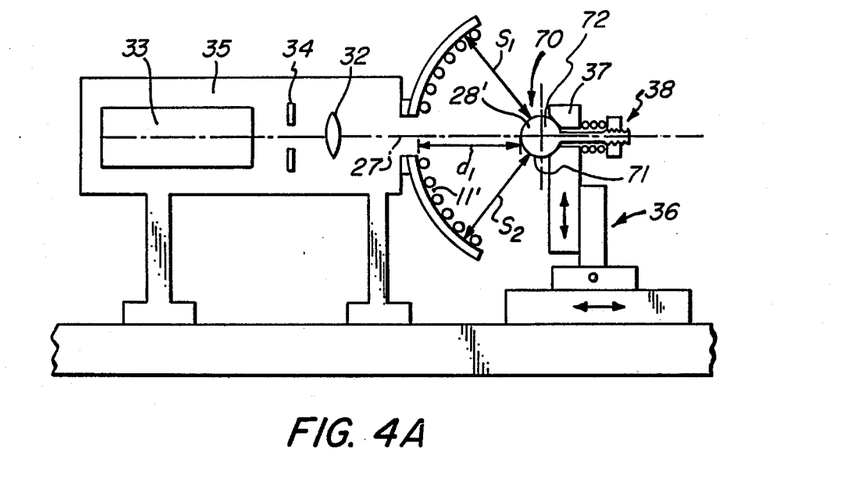
FIG. 4A is a simplified optical diagram of apparatus of FIG. 1, arranged in a calibrating mode.

The location for each luminous point $P_2$ must be known in order for the last described computational process to be used. These locations can be determined by directly measuring the coordinates of each LED source of the array 11. Alternatively, and preferably, this location can be determined with a calibration device 70. The calibration device includes a surface 71 of known contour. This surface 71 may comprise a spherical surface. A preferred technique of performing the calibration of apparatus 35 is accomplished by inserting a substantially spherical member 72 having a spherical surface 28' of precisely known radius into the apparatus 36. The spherical member 72 is located with its center on axis 27 at distance $d_1$ from surface 11A, as shown in FIG. 4A. The spherical member 72 can be positioned in the axial direction and in two transverse directions with respect to topography measuring apparatus 35, using adjusting means 36 which may typically comprise a three-dimensional translation stage. Proper centering is indicated by equality of the dimensions $S_1$ and $S_2$ to each other in the plane of FIG. 4A, as well as in the plane which includes axis 27 and is perpendicular to FIG. 4A. Adjustments to locate surface 28' at the specified distance $d_1$ from the spherical LED Locus (surface 11) can be accomplished by the linear adjustment means of fixture 36. Once initially aligned, a conical seat 37 and a spring-loaded clamping means 38 provide a convenient and reliable means for relocating the spherical member 72 at its prescribed location, whenever calibration is to be rechecked.

Figures 4B, 5A, 5B, 5C, 6:
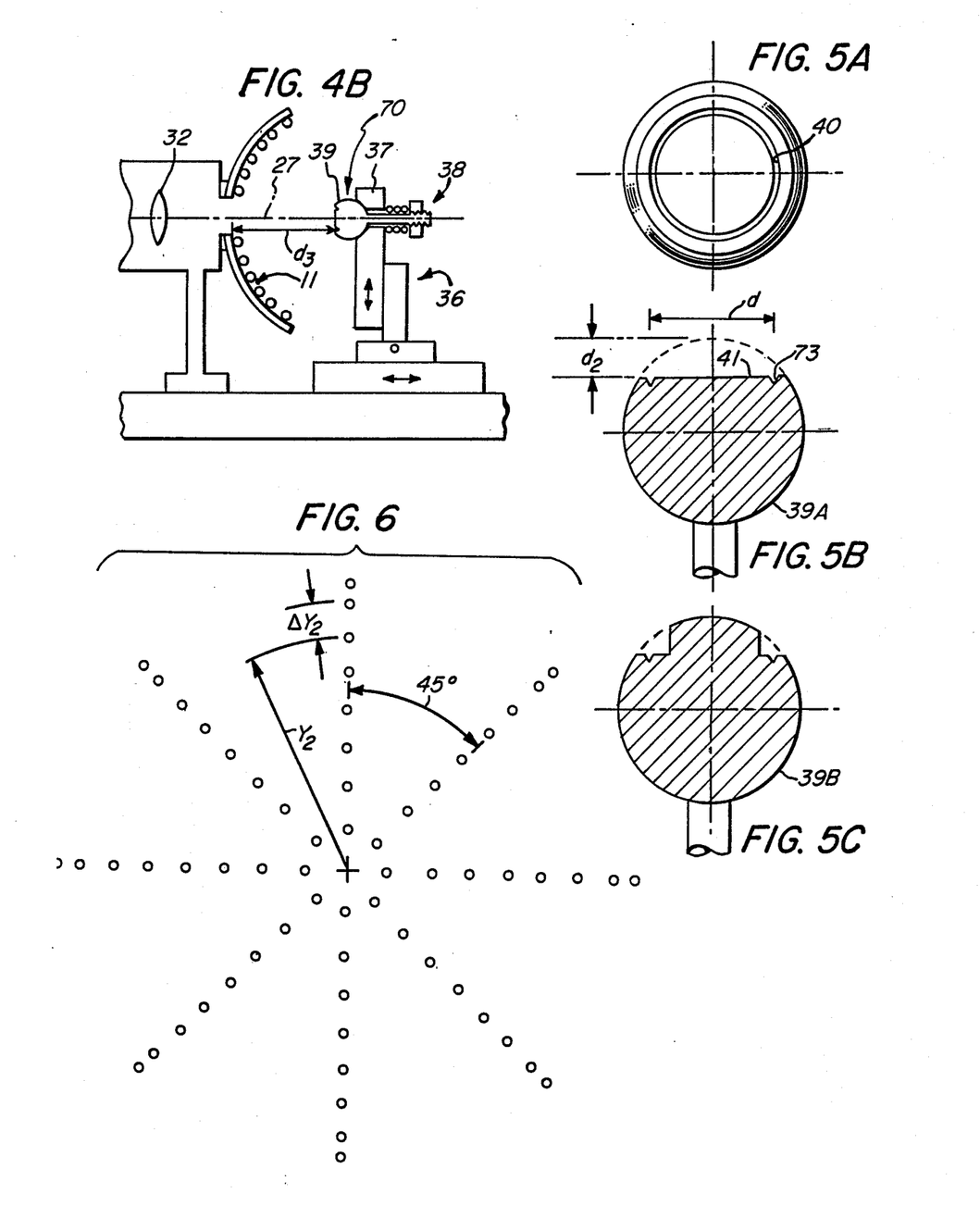
FIG. 4B is a similar but fragmentary diagram to illustrate a modification.
FIGS. 5A and 5B are respectively front-end and longitudinal-section views, to an enlarged scale, for a calibration element in FIG. 4B.
FIG. 5C is a modified calibration element.
FIG. 6 is a representation, in a radial-plane projection, for an illustrative distribution of multiple light sources in the array of FIG. 2.

In order to use the reflecting spherical member 72 as a calibration means, or to use the corneascope-type apparatus 35 to determine the topography of a cornea under test, the magnification of lens 32 must be known. This parameter can be measured as indicated in FIG. 4B, where a fiducial target member 39 is inserted in the adjustable fixture means 36 against the seat 37 at an axial distance $d_3$ from surface 11A. Then, a determination is made of the size of the corresponding image of the surface of target 39 on photodetecting means 19. The ratio of the measured image dimension to the actual object dimension is the magnification of the optical system, or lens 32. Typically, the absolute value of said magnification is about 0.4 to 0.6 times.

The ideal value of $d_3$ is slightly greater than $d_1$ since target surface 41 should be located essentially at the same distance from lens 32 as the image of the LEDs reflected by convex surface 28. The latter image is virtual and located at a distance behind said surface 28 given by the expression:

$$d_2 = (R_1 d_1)/(2d_1 + R_1) \tag{5}$$

Typically, for $d_1 = 100$ mm and $R_1 = 8$ mm, $d_2 = 4.2$ mm and $d_3 = d_1 + d_2 = 104.2$ mm. This location of the fiducial target surface 41 ensures that the images at the photodetector 19 of the LEDs and of the fiducial target will both be in focus.

By virtue of the telecentric nature of the optical system in object space of the lens 32, the magnification is essentially constant for moderate variations (of the order of a few millimeters) in the distance $d_1$. Since the location of a given point on the photosensitive surface of photodetecting means 19 is generally derived by measuring the distance of the point in units of pixel (picture element) widths horizontally and pixel heights vertically from some reference (such as a corner of the rectangular raster), and since the dimensions of a typical pixel may be different in these directions, the linear magnifications in these two directions may differ from each other. The measured values would generally be stored in computer memory for use at appropriate times during the subsequent computations.

The fiducial target 39 may be any of a variety of types such as two or more separated marks 73 so designed as to reflect or absorb light thereby becoming visible due to contrast against the background formed by the underlying surface of the target substrate. Since magnification can vary azimuthally about the axis 27 of an optical system, it is advisable to have dual fiducial marks on each of at least two mutually perpendicular intersecting diameters. In a preferred simple embodiment, a circular fiducial ring 40 is scribed or otherwise marked on the fiducial target substrate 39. The ring 40 is then located so as to be concentric with the axis 27, as indicated in FIGS. 5A and 5B. The fiducial ring 40 may be generated on a flattened surface 41 of an otherwise spherical target body 72, e.g., a flat locally ground on a tooling or bearing ball. It can then easily be seated against the conical seat 37 of the adjusting means 36 of FIG. 4B, thereby assuring proper centering with respect to the spherical LED locus 11 and to the axis 27. The depth of material removed in generating the flattened surface of the fiducial target on a sphere of radius $R_1$ is equal to the aforementioned dimension $d_2$.

As indicated in FIG. 5C, the functions of the spherical reflecting calibration surface 28' and of the fiducial target 39 can be combined as at 39B by suitably machining a spherical ball.

In a calibrating use, the LED sources are illuminated and the corresponding locations of the images at the image sensor 19 determined in the same manner as for the corneal reflections previously described. After converting these images to corresponding heights $Y_1$, the actual X and Y coordinates of the points $P_2$ for all the LEDs can be computed. This is the self-calibration process referred to as one object of the invention.

The method for accomplishing this computation also relies upon the law of reflection at surface 28 and mathematical expressions derived from analytic geometry, as follows:

$$Y_2^4 + I\,Y_2^3 + J\,Y_2^2 + L\,Y_2 + M = 0; \tag{6}$$

where:

$$H = 4\,K_2^2 + K_3^2$$

$$I = (4K_2K_3R_2 + 2\,K_3K_4 + 8K_1K_2)/H$$

$$J = (4\,K_1^2 + 4K_1K_3R_2 + 4K_2K_4R_2 + 2K_3K_5 + K_4^2)/H$$

$$L = (4\,K_1K_4R_2 + 4\,K_2K_5R_2 + 2\,K_4K_5)/H$$

$$M = (4\,K_1K_5R_2 + K_5^2)/H$$

$$K_1 = (X_c - X_1)Y_1^2$$

$$K_2 = (X_1 - X_c)Y_1$$

$$K_3 = Y_1^2 - X_c^2 + 2X_cX_1 - X_1^2$$

$$K_4 = 2(X_c^2 Y_1 - X_c X_1 Y_1 - Y_1^3)$$

$$K_5 = Y_1^4 + X_1^2 Y_1^2 - X_c^2 Y_1^2$$

Once the $Y_2$ values have been computed, it is a simple matter to compute the corresponding $X_2$ values from the expression:

$$X_2 = \sqrt{R_2^2 - Y_2^2} \tag{7}$$

where $R_2$ is the known radius of curvature of the spherical locus of all the LED sources (i.e., points $P_2$).

This feature of the present invention allows the corneascope to be calibrated thereby negating the deleterious effects of unavoidable manufacturing uncertainties in locations of the LED light sources used in calculating the corneal radius. By accomplishing this calibration periodically, instrument errors can be reduced to a minimum, and the resultant precision in measuring radius of curvature and dioptric power at a given point on the cornea is improved significantly over that achieved with prior art methods and apparatus.

In order to provide radius information at an adequate number of points over the circular area of interest on the cornea (typically of 5 to 7 millimeters diameter, centered on the optical axis of the eye) for ophthalmic diagnosis purposes, the light-source array 11 preferably includes many individual point light sources. FIG. 6 illustrates such an array comprising 64 LEDs arranged as 4 rows of 16 LEDs each crossing the aperture of the array, along meridians oriented at 45-degree intervals of azimuthal angle. The LEDs are located on a concave spherical surface to minimize the overall size of the apparatus while providing the required angular inclination of narrow beams from the individual sources to the subsequent optical elements in the system. It will be understood that additional light sources can be included along each meridian in the array, or additional meridians can be added in total or in part, if more information about the corneal contour is needed; conversely, fewer light sources may be used if less information is needed. In an alternate embodiment, a full complement of many light sources could be installed, but specific geometric groupings of sources could be selected by a suitable switching arrangement (not shown) to fit the need of a particular measurement to be accomplished at any time, thereby reducing the overall time required for processing and analysis of the data.

As was pointed out earlier in this description, the physical aperture diameter of the telecentric stop (iris) 34 can be quite small and yet allow sufficient light to pass through the system to produce detectable images on the photosensing means 19. Calculations pertinent to a particular embodiment of the invention indicate that, for image quality reasons, the image-forming beam should have an effective relative aperture no larger (i.e., no faster) than f/13. This has a secondary effect upon the performance of the image-forming system in that it significantly increases the depth of field for the LEDs and allows sharp images thereof to be formed at all points within the field of view. Some prior art systems used for this purpose have exhibited degraded image sharpness at edges of their field of view due to uncorrected aberrations related to the large effective relative aperture used therein.

The radial distance $Y_2$ indicated for a typical LED in FIGURE 6 corresponds to the Y coordinate of point $P_2$ in FIG. 3, and it will be noted that radial separations ( $Y_2$) between LEDs along any meridian are not constant. This circumstance reflects the preferred condition of equal radial separations ( $Y_1$) of adjacent incidence points $P_1$ for the principal rays on surface 28. If the surface 28 is spherical, the corresponding radial separations of image points in the image plane at photo-detecting means 19 also are equal. While not essential to the function of the apparatus, this equality of image spacing facilitates detection of surface 28 irregularities, including astigmatism, when the composite image of the entire LED array is observed on the display 22 of FIG. 1 or is shown in hard copy produced by printer 25.

Figure 7:
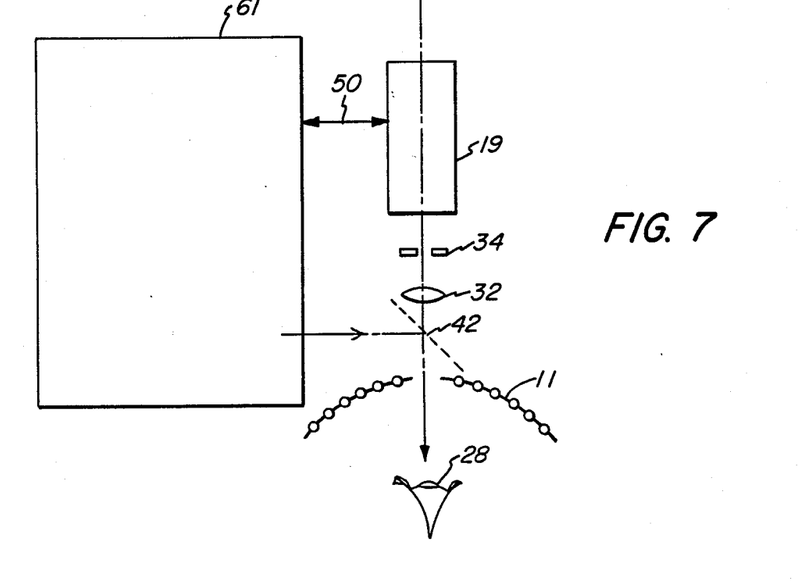
FIG. 7 is a diagram to illustrate use of the invention in conjunction with apparatus for surgical sculpture of the cornea.

In FIG. 7, the invention is shown in simplified form, interfacing directly (via a fold mirror 42) with laser-sculpturing apparatus 61 of the general type described by Telfair, et al., in patent applications Ser. No. 928,633 and Ser. No. 009,724. When the fold mirror 42 is removed from the beam, the present corneascope-type topography measuring device can be used to evaluate the contour of the cornea 28 located near the center of curvature of the array 11. If a beamsplitter is used in lieu of the mirror 42, the diagnostic function can be accomplished in near-real time with laser sculpturing. In either of these events, a synchronizing connection 50 is shown between the sculpturing apparatus 61 and the photosensitive device 19 of the topography measuring apparatus, to assure at least an interlaced separation of sculpturing versus measuring functions in the course of a given surgical procedure.

Inasmuch as the image formed by lens 32 on photodetecting means 19 is not limited to the specific 5 to 7 millimeter diameter area of interest in diagnostic evaluation of the topography of the cornea, the described apparatus can be used to observe a large portion of the exterior of the eye under magnification, as in a surgical microscope.

Figure 8:
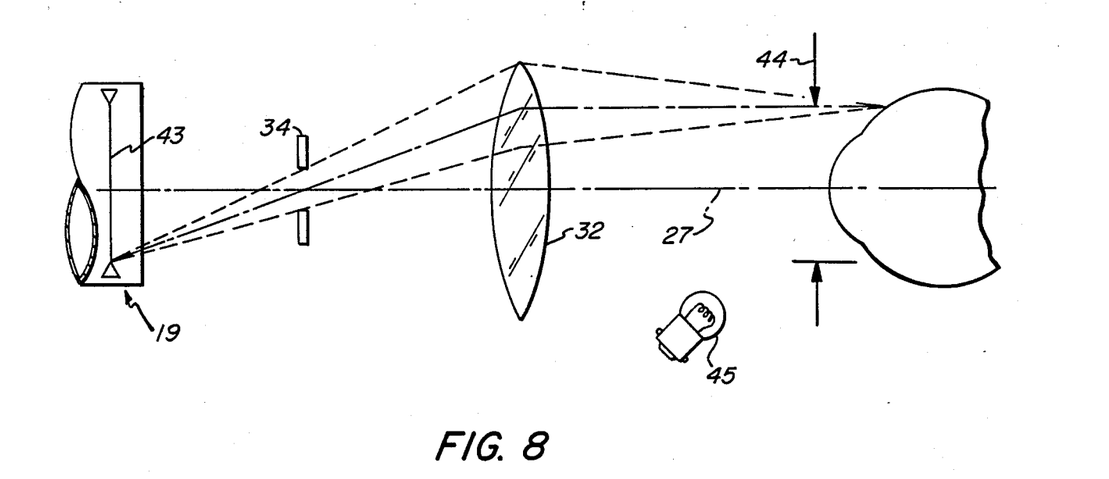
FIG. 8 is an optical diagram to show another application of the invention.

As depicted in FIG. 8, the field of view of the optical system is determined by the angular subtense of the sensitive area 43 on photodetector 19, as measured from the center of the aperture stop 34. Typically, the extent 44 of said field of view at the eye under examination is 12 to 16 millimeters in diameter, depending upon the specific combination of parameters in the design.

The image of the eye is presented in real time to the observing ophthalmologist and to other interested parties via the video subsystem comprising the vidicon or CCD array 19, signal switch 21 and display 22. Illumination of the eye is provided by a light source 45 which will be understood to be a single lamp or a multiplicity of lamps, e.g., room lights. By use of appropriate video components, the display can be presented in monochrome (i.e., black and white) or in true or false color.

Inherent in successful functioning of the invention is establishment of the proper axial distance $d_1$ (see FIG. 3) between the light source 11 and the surface under test 28. Mathematical analysis clearly shows that, in order to achieve $\pm\frac{1}{4}$ diopter precision in corneal refractive power measurements, the dimension $d_1$ must be held constant within approximately $\pm 0.25$ mm of the design value during calibration and operation.

This level of distance measurement and control can be achieved in a variety of ways. For example, a simple mechanical probe of calibrated length can be extended from the topography measuring apparatus to just touch the surface 28 at its axial vertex when said surface is at the proper location. The possibility of damaging the test surface with a probe precludes its application to ophthalmic applications. Non-contacting (optical or electro-optical) means such as ones functioning in a range-finding mode in cameras to establish focus or means using inclined projected light beams which superimpose when incident upon the test surface if said surface is located at the proper (precalibrated) axial distance or means which illuminate a multielement detector array be reflected specular or scattered light can typically be applied here.

A simple, preferred, non-contacting means for focus sensing employs an optical microscope (commonly called a "telemicroscope") with a long working distance, i.e. the clearance between object observed and the nearest surface of the microscope, so oriented as to allow the surface 28 to be seen in profile from a direction normal to the optical axis of the topography measuring apparatus. By attaching this telemicroscope to the topography measuring apparatus in stable fashion, so its line of sight does not change location with time, it can be utilized as a fixed reference for focus distance measurement. The telemicroscope can also be used to establish the proper focus distance to either the calibration ball 70 or to the tested surface 28 to ensure applicability of the calibration to the specific test surface evaluation.

Figure 9:
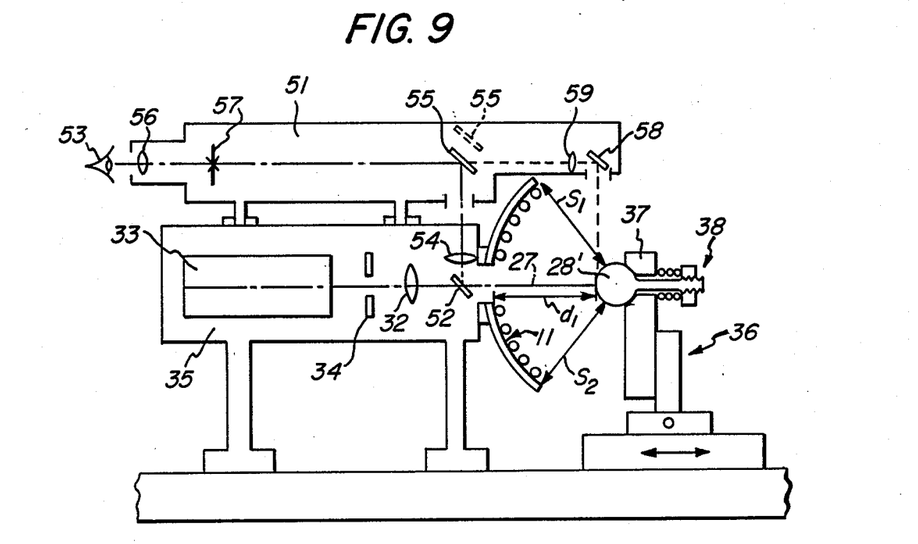
FIG. 9 is a further development of FIG. 4A incorporating means to measure alignment of the eye calibration device relative to the diagnostic apparatus.

FIG. 9 illustrates schematically one embodiment of the focus alignment sensing device 51, i.e. a telemicroscope, integrated into the corneal topography measuring apparatus 35. In this embodiment, means are provided for the user's eye 53 to observe a view along the axis 27 of the reflected pattern of LED images from surface 28' via beamsplitter 52, lens 54, mirror 55A, and eyepiece 56. Alignment reference is achieved by internal means such as a cross-hair reticle pattern 57 located at the image of the LED pattern. In use during calibration, this optical subsystem allows the surface 28' to be centered vertically and horizontally through action of adjustable fixture 36. In use during measurement of a cornea, this subsystem provides a reference for vertical and horizontal alignment of the vertex of the eye through action of appropriate mechanisms which adjust position of the subject's head and/or eye.

Figure 10:
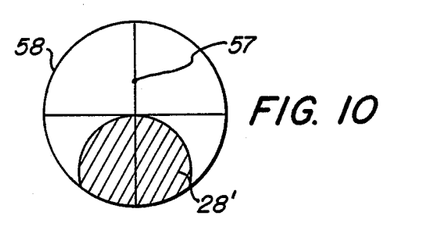
FIG. 10 shows the typical appearance of the visual field of the focus alignment sensing means in the calibration mode.
Figure 11:
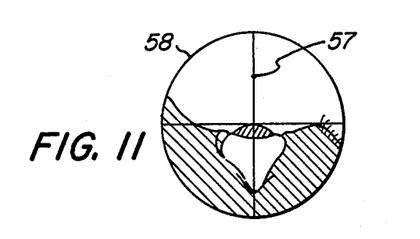
FIG. 11 shows the typical appearance of the visual field of the focus alignment sensing means in the operational mode.

Another feature of the apparatus shown in FIG. 9 is the alternate telemicroscope path formed by movement of mirror 55A out of the above-described optical path to a position such as is shown at 55B. An image of a side view of surface 28' or of the surface under tests will then be accessed by means of mirror 58 and lens 59 used in conjunction with the remaining components of the basic telemicroscope. The appearance of the field of view of said adapted telemicroscope in the focus measurement mode during calibration is illustrated schematically in FIG. 10. A similar view showing proper alignment of the eye cornea to the telemicroscope's crosshair pattern is shown in FIG. 11. It should be noted that it is preferable, but not essential, that the image presented to the operator's eye be erect since this would facilitate use of the device.

Figure 12:
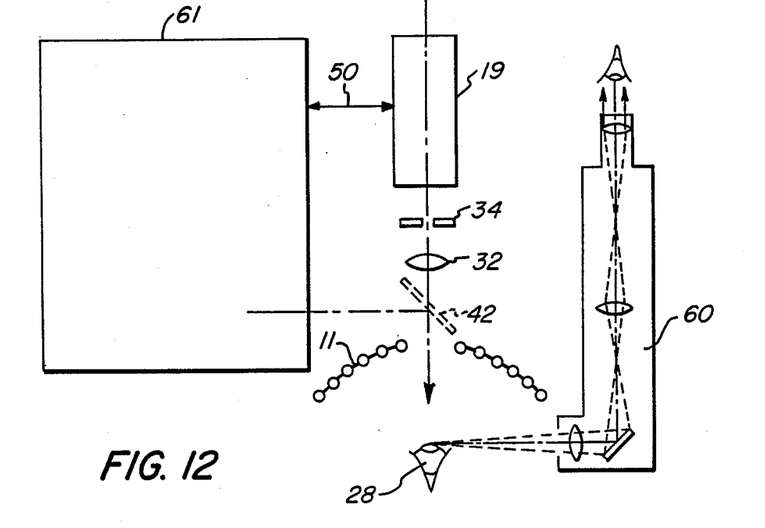
FIG. 12 is a simplified diagram relating the focus alignment sensing means to a laser sculpturing apparatus.

FIG. 12 represents one embodiment of an image-erecting focus alignment measuring telemicroscope means 60 incorporated by mechanical structure, not shown, into a laser sculpturing apparatus 61 which is equipped with a corneal topography measuring apparatus of the type described here.

While the present invention has been described primarily for use in measuring the contour of a cornea, it can also be used to measure the shape of any regular or irregular contoured surface. For example, the invention could be used to measure the contour of optical lenses, mirrors, ball bearings and precision machine parts, to name a few.

The patents and patent applications set forth in this application are intended to be incorporated by reference herein.

It is apparent that there has been provided in accordance with this invention a method and apparatus for measuring the topography of a contoured surface which satisfies the objects, means, and advantages set forth hereinabove. While the invention has been described in combination with the embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A contour measuring apparatus to measure the three-dimensional contour of a surface, comprising:
   a contour measuring structure having a multi-point light source to direct a plurality of individual light beams each corresponding to individual light points of the multi-point light source onto the surface being measured, said surface being the anterior surface of a cornea;
   a photodetector receiving reflections of the individual light beams from said surface for generating electrical output signals corresponding to electro-optically measurable optical images, each of said images corresponding to one of said light points;
   means disposed between said surface being measured and said photodetector for focusing the reflected beams of light from the surface being measured onto the photodetector to form the measurable optical images;
   means between the focusing means and said photodetector for limiting the cone angle of the rays of the individual light beams reflected from the surface whereby each of said reflected rays closely approximates a telecentric principal ray corresponding to a light point;
   said focusing means comprising a lens having an optical axis extending through said contour measuring structure;
   said photodetector including a photodetector surface into which said reflected light beams are focused, said photodetector surface being disposed transverse to said optical axis;
   means receiving said electrical output signals from said photodetector for measuring the position of each optical image in the photodetector and for determining both the local radius of curvature of the measured surface at each point of incidence of the individual corresponding light beams and the average radius of curvature of the measured surface;
   calibration means for reducing instrument errors of the apparatus, said calibration means including:
      a calibration surface with a known contour to be positioned in substitution of said surface being measured;
      means for determining the magnification of said lens; and
      fiducial target means on the calibration surface being reflected as a fiducial target image onto the photodetector whereby comparison of the size of the reflected fiducial target image with the actual fiducial target image enables the magnification of said lens to be determined.

2. The apparatus of claim 1 in which said means for limiting the cone angle comprises a telecentric aperture stop positioned between said lens and said photodetector substantially at the focal point of said lens.

3. The apparatus of claim 2 in which the telecentric aperture stop limits the cone angle of the light beams reflected from the surface being measured to produce uniformly sharp images of the reflected beams on the photodetector surface.

4. The apparatus of claim 3 further including a video monitor connected to said photodetector for display of the images of the reflected beams on the photodetector surface, said video monitor including means for image-display expansion whereby an enlarged image of the illuminated exterior of the measured surface can be presented in monochrome or color on the video monitor.

5. The apparatus of claim 2 further including means to determine and store in memory the location of each individual light point on said multi-point light source.

6. The apparatus of claim 5 wherein said means to determine and store include a frame grabber.

7. The apparatus of claim 6 wherein said means to determine both the local radius of curvature and the average radius of curvature includes computer means.

8. The apparatus of claim 7 wherein said individual light points comprise an array of individual LEDs.

9. The apparatus of claim 8 further including selectively operable means associated with said computer means to select a particular group of LED images for analysis and evaluation to the exclusion of other groups of images at the photodetector surface.

10. The apparatus of claim 8 further including means to select the number of discrete LED sources employed in a given measurement whereby selection may be made to a minimum number, consistent with specific requirements for accuracy and spatial distribution of data on the measured surface thereby reducing the elapsed time required for data analysis.

11. The apparatus of claim 10 wherein said calibration surface is substantially spherical.

12. The apparatus of claim 11 wherein the spherical calibration surface is polished.

13. The apparatus of claim 11 wherein said calibration means includes means for independently adjusting the position of the calibration surface in each of three orthogonally related axes of displacement to facilitate mutual alignment of the calibration surface with the optical axis through the apparatus and to set the axial focus position of the calibration surface with respect to the focusing means.

14. The apparatus of claim 13 further including means to support a spherical surface.

15. The apparatus of claim 14 wherein said calibration means includes means for independently adjusting the position of the calibration surface in each of three orthogonally related axes of displacement to facilitate mutual alignment of the calibration surface with the optical axis through the apparatus and to set the axial focus position of the calibration surface with respect to the focusing means.

16. The apparatus of claim 1 further including optical means to provide a measurable reference when setting the axial focus position of the surface being measured with respect to the focusing means.

17. The apparatus of claim 16 wherein said optical means includes a video camera producing an image of the surface being measured on a monitor where it can be observed by the operator.

18. The apparatus of claim 17 wherein said optical means further includes mirror means to access an image of the surface being measured.

19. The apparatus of claim 16 wherein said optical means is a telemicroscope delivering an image of the surface being measured to the operator's eye.

20. The apparatus of claim 19 wherein said optical means further includes mirror means to access an image of the surface being measured.

21. The apparatus of claim 16 including:
laser-sculpturing apparatus having an axis of sculpturing laser-beam delivery;
an optical element disposed so as to place the axis of laser beam delivery in coincidence with the optical axis of the contour-measuring structure whereby said laser-sculpturing apparatus and said contour-measuring structure are interconnected for combined individual laser-sculpting and cornea-evaluation operation.

22. The contour measuring apparatus of claim 21 wherein said means for determining includes means for computing and storing in memory the location of each individual light point.

23. The contour measuring apparatus of claim 22 including the step of determining the average radius of curvature of the measured surface, the extreme long and short radii of said measured surface, the dioptric equivalent of each of said radii, the difference in the average optical powers on the directions of the principal astigmatic meridians, and the azimuthal orientations of said meridians.

24. A contour measuring apparatus to measure the three-dimensional contour of a surface, comprising:
a contour measuring structure having a multi-point light source to direct a plurality of individual light beams each corresponding to individual light points of the multi-point light source onto the surface being measured;
a photodetector receiving reflections of the individual light beams from said surface for generating electrical output signals corresponding to electro-optically measurable optical images, each of said images corresponding to one of said light points;
means disposed between said surface being measured and said photodetector for focusing the reflected beams of light from the surface being measured onto the photodetector to form the measurable optical images; said focusing means comprising a lens centered on an optical axis extending through said contour measuring structure;
means between the focusing means and said photodetector for limiting the cone angle of the rays of the individual light beams reflected from the surface whereby each of said reflected rays closely approximates a telecentric principal ray corresponding to a light point;
said photodetector including a photodetector surface into which said reflected light beams are focused, said photodetector surface being disposed transverse to said optical axis;
means receiving said electrical output signals from said photodetector for measuring the position of each optical image in the photodetector and for determining both the local radius of curvature of the measured surface at each point of incidence of the individual corresponding light beams and the average radius of curvature of the measured surface; and
calibration means for reducing instrument errors of the apparatus, said calibration means including:
a calibration surface with a known contour to be positioned in substitution of said surface being measured; and
means for determining the magnification of said lens whereby the curvature of the measured surface can be determined.

25. The apparatus of claim 1 wherein said fiducial target means comprises a primary spherical calibration means having a flat surface with at least two separated marks thereon.

26. The apparatus of claim 25 wherein said at least two separated marks are disposed on at least two mutually perpendicular intersecting diameters.

27. The apparatus of claim 1 wherein said fiducial target means comprises a circular ring marked onto a flat calibration surface, said ring being concentric with optical axis.

28. A contour measuring apparatus to measure the three-dimensional contour of a surface, comprising:
   a contour measuring structure having a multi-point light source to direct a plurality of individual light beams each corresponding to individual light points of the multi-point light source onto the surface being measured, said surface being the anterior surface of a cornea;
   a photodetector receiving reflections of the individual light beams from said surface for generating electrical output signals corresponding to electro-optically measurable optical images, each of said images corresponding to one of said light points;
   means disposed between said surface being measured and said photodetector for focusing the reflected beams of light from the surface being measured onto the photodetector to form the measurable optical images, said focusing means comprising a lens centered on an optical axis extending through said contour measuring structure;
   means between the focusing means and said photodetector for limiting the cone angle of the rays of the individual light beams reflected from the surface whereby each of said reflected rays closely approximates a telecentric principal ray corresponding to a light point;
   means receiving said electrical output signals from said photodetector for measuring the position of each optical image in the photodetector and for determining both the local radius of curvature of the measured surface at each point of incidence of the individual corresponding light beams and the average radius of curvature of the measured surface;
   a laser-sculpturing apparatus having an axis of sculpturing laser-beam delivery;
   a beam splitter disposed so as to place the axis of laser-beam delivery in coincidence with the optical axis through said contour measuring structure so that said laser-sculpturing apparatus and said contour-measuring structure are interconnected for combined individual laser-sculpting and cornea-evaluation operations.

29. The method of measuring a surface, comprising the steps of:
   directing a plurality of individual light beams each corresponding to individual light points of a multi-point light source onto the surface being measured;
   providing a photodetector for generating electrical output signals corresponding to electro-optically measurable optical images;
   focusing the reflected beams of light from the measured surface onto the photodetector to form measurable optical images, each of said images corresponding to one of each light points, said step of focusing the reflected beams of light including the steps of:
   disposing a lens transverse to an optical axis extending from said surface being measured to said photodetector;
   directing the beams of light through said lens;
   limiting the cone angle of the reflected beams of light whereby each individual beam closely approximates a telecentric principal ray of individual beam;
   measuring the position of each optical image on the photodetector from the electrical output signals of the photodetector for determining both the local radius of curvature of the measured surface at each point of incidence of the individual light beams and average radius of curvature of the measured surface; and
   prior to the step of determining the radius of curvature of the measured surface, reducing the instrument errors of the apparatus using the following steps:
   substituting the surface to be measured with a calibration surface having a known contour; and
   determining the magnification of the lens whereby the curvature of the measured surface can be determined.

30. The method of claim 29 wherein the step of limiting the cone angle of the reflected beams further includes the step of directing the focused reflected beams of light through a telecentric aperture stop positioned on said optical axis between the lens and the photodetector at the focal point of the lens.

31. The method of claim 29 further comprising the step of measuring the contour of a surface selected from the group comprising corneas, optical lenses, mirrors, ball bearings and precision machine parts.

32. The method of claim 29 further including the step of determining and storing in memory the location of each individual light point.

33. The method of claim 29 wherein the step of determining the local radius of curvature includes the step of:
   computing the local radius of curvature of the measured surface at each point of coincidence of the individual light beams, as a function of the height from the optical axis through the apparatus to the point at which a beam intercepts the measured surface $Y_1$ and the distance from the origin "0" of the individual light points to the measured surface $X_1$, the radius of curvature at the interception point of the beam with measured surface $R_1$ substantially according to the formula $$R_1 = \sqrt{Y_1^2 + X_1^2}$$

34. The method of claim 33 including the steps of computing the average radius of curvature of the measured surface, the extreme long and short radii of said measured surface, the dioptric equivalent of each of said radii, the difference in the average optical powers of the directions of the principal astigmatic meridians, and the azimuthal orientations of said meridians.

35. The method of measuring the three-dimensional contour of the surface of a cornea, comprising the steps of:
   providing a multi-point light source;
   directing a plurality of individual light beams each corresponding to individual light points of a multi-point light source onto the corneal surface being measured, said surface being the anterior surface of a cornea;

providing a photodetector for generating electrical output signals corresponding to electro-optically measurable optical images;

focusing the reflected beams of light from the corneal surface being measured onto the photodetector along an optical axis extending from the measured surface to the photodetector to form the measurable optical images, each of said images corresponding to one of said light points;

limiting the cone angle of the rays of the individual light beams reflected from the surface whereby each of said reflected rays closely approximates a telecentric principal ray corresponding to a light point measuring the position of each optical image on the photodetector from the electrical output signals of said photodetector for determining both the local radius of curvature of the measured corneal surface at each point of incidence of the individual corresponding light beams and the average radius of curvature of the measured surface;

providing a laser-sculpturing apparatus having an axis of sculpturing laser-beam delivery for laser sculpturing of corneas;

disposing a beam splitter so as to place the axis of laser-beam delivery in coincidence with the optical axis from the measured surface to the photodetector for combined individual laser-sculpting and cornea-evaluation operations.

* * * * *